US012611553B2

(12) United States Patent
Xiang et al.

(10) Patent No.: US 12,611,553 B2
(45) Date of Patent: Apr. 28, 2026

(54) SYSTEM AND METHOD OF XACT/US-GUIDED RADIOTHERAPY

(71) Applicant: The Regents of the University of California, Oakland, CA (US)

(72) Inventors: Liangzhong Xiang, Oakland, CA (US); Siqi Wang, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 157 days.

(21) Appl. No.: 18/249,051

(22) PCT Filed: Oct. 13, 2021

(86) PCT No.: PCT/US2021/054858
§ 371 (c)(1),
(2) Date: Apr. 13, 2023

(87) PCT Pub. No.: WO2022/081763
PCT Pub. Date: Apr. 21, 2022

(65) Prior Publication Data
US 2023/0405361 A1     Dec. 21, 2023

Related U.S. Application Data

(60) Provisional application No. 63/091,590, filed on Oct. 14, 2020.

(51) Int. Cl.
*A61N 5/10*          (2006.01)
*A61B 5/00*          (2006.01)
(Continued)

(52) U.S. Cl.
CPC .......... *A61N 5/1049* (2013.01); *A61B 5/0093* (2013.01); *A61B 6/4417* (2013.01); (Continued)

(58) Field of Classification Search
CPC ...... A61N 5/1049; A61N 5/1064–1071; A61B 5/0093
See application file for complete search history.

(56) References Cited

U.S. PATENT DOCUMENTS

| | | | |
|---|---|---|---|
| 2011/0088477 A1 | 4/2011 | Someda et al. | |
| 2022/0212036 A1* | 7/2022 | Naqa | A61B 8/485 |

OTHER PUBLICATIONS

Lee, Wonseok, and Yongrae Roh. "Ultrasonic transducers for medical diagnostic imaging." Biomedical engineering letters 7.2 (2017): 91-97.*

(Continued)

*Primary Examiner* — Carolyn A Pehlke
(74) *Attorney, Agent, or Firm* — FOLEY & LARDNER LLP

(57)          ABSTRACT

Embodiments are directed to a new imaging modality called X-ray-induced acoustic computed tomography (XACT) technology and can be combined with traditional pulse and echo ultrasound imaging. It has the capability of real-time monitoring of geometric and morphological misalignments of the X-ray field with respect to the target tissue, thus improving radiotherapy tumor eradication and limiting treatment side effects. The XACT/US image-guided radiotherapy system according to embodiments holds great potential for personalized cancer treatment and better outcomes.

11 Claims, 7 Drawing Sheets

(51) Int. Cl.
    *A61B 6/00*         (2024.01)
    *A61B 8/00*         (2006.01)

(52) U.S. Cl.
    CPC .... *A61B 8/4416* (2013.01); *A61N 2005/1058*
             (2013.01); *A61N 2005/1061* (2013.01)

(56)               References Cited

OTHER PUBLICATIONS

International Search Report and Written Opinion for PCT Application No. PCT/US2021/054858 dated Dec. 28, 2021 (8 pages).
Zhang et al., "Dual-Modality X-Ray-Induced Radiation Acoustic and Ultrasound Imaging for Real-Time Monitoring of Radiotherapy," BME Frontiers, vol. 2020, May 26, 2020, Article ID 9853609, 10 pages, https://doi.org/10.34133/2020/9853609.

* cited by examiner

SYSTEM AND METHOD OF
XACT/US-GUIDED RADIOTHERAPY

CROSS-REFERENCE TO RELATED
APPLICATIONS

The present application is a National Stage Entry under 35 U.S.C. § 371 of International Application No. PCT/US2021/054858, filed Oct. 13, 2021, which claims priority to U.S. Provisional Patent Application No. 63/091,590 filed Oct. 14, 2020, the contents of which are incorporated herein by reference in their entirety.

TECHNICAL FIELD

The present embodiments relate generally to X-ray-induced Acoustic Computed tomography (XACT), in vivo dosimetry, and multi-dimensional dosimetry, and more particularly to a system and method to increase the precision of radiotherapy by visualizing the radiation beam with respect to positions of the tumor and other surrounding normal tissues.

BACKGROUND

Cancer is a major public health concern and a leading global cause of death. Radiation therapy is one of the most common treatments for cancer. Radiation dosimetry is a crucial process in radiation therapy to ensure that the correct dose is accurately delivered to the desired location. However, in such a widely used clinical intervention, the delivered radiation dose can only be planned and/or verified via simulation with phantoms, and an in vivo and in-line verification of the delivered dose is still absent in the clinic.

Using modern dose calculation algorithms, dose prediction in treatment planning is highly accurate. However, verification of delivery is especially important in many fields such as dynamic delivery intensity modulated radiotherapy (IMIRT) and volumetric modulated arc therapy (VMAT), where failure to deliver the planned dose can result in disastrous consequences. These plans use small beams and steep gradients, rendering conventional detectors, such as a Farmer ionization chamber, inadequate. Gel dosimetry has become a tool for moderately accurate dosimetry in a tissue equivalent or anthropomorphic geometry, but material-specific and readout errors, as well as long readout times, prevail. Diode array-based systems are perhaps the industry standard for verification of individual plans, but these have distinct limits on spatial resolution. Transit dosimetry based upon reconstructing the dose inside a phantom portal can retrieve images, but still requires a simulation-based scatter correction for accuracy and/or other assumptions about the beam depth-dose curve in the media. Recently, Cherenkov emission was found to be useful for in vivo radiation dose mapping, and a radioluminescence imaging technique also developed for quality assurance (QA), but this is only suitable for surface dosimetry applications.

Therefore, there is a great need for the development of high-resolution (<3 mm, a typical tumor margins in radiotherapy of prostate cancer in clinic) 3D in vivo dosimetry techniques for real time monitoring of the radiation dose in patients during radiation therapy.

SUMMARY

Embodiments are directed to a new imaging modality, referred to herein as X-ray-induced acoustic computed tomography (XACT) technology, which can be combined with traditional pulse and echo ultrasound imaging (i.e. XACT/US). It has the capability of real-time monitoring of geometric and morphological misalignments of the X-ray field with respect to the target tissue, thus improving radiotherapy tumor eradication and limiting treatment side effects. The XACT/US image-guided radiotherapy system according to embodiments holds great potential for personalized cancer treatment and better outcomes.

BRIEF DESCRIPTION OF THE DRAWINGS

These and other aspects and features of the present embodiments will become apparent to those ordinarily skilled in the art upon review of the following description of specific embodiments in conjunction with the accompanying figures, wherein:

FIG. 1a illustrates an example multi-leaf collimator produced field pattern at 100 cm source to surface distance, where the primary beam is located on the white region. FIG. 1b illustrates an example experimental XACT image of the photon beams in a water tank at 10 cm depth. FIGS. 1c and 1d show two examples of an XACT image of the location of the beam overlapped with an ultrasonic image of a liver with a square of fat simulating a tumor.

DETAILED DESCRIPTION

According to certain aspects, the present embodiments enable in vivo dosimetry for the end-user: medical physicists. It is expected that X-ray-induced acoustic computed tomography (XACT) can be used for in-line verification of photon beam location and dose in cancer patients. In X-ray-induced acoustic phenomena, X-rays are absorbed and converted to heat; subsequent thermoelastic expansion generates an acoustic wave, which can be imaged by acoustic detectors. Further, the generated acoustic signal strength is linearly proportional to the X-ray dose deposition; this feature enables the X-ray induced signal to monitor radiation dosage during radiation therapy.

According to certain additional aspects of the present embodiments, adding pulse and echo ultrasound imaging on top of XACT imaging (i.e. XACT/US), the medical physicist can monitor the geometric and morphological misalignments of the X-ray field with respect to the target tissue in real-time. These and other embodiments have the ability to expand the current clinical paradigm towards high-precision radiotherapy.

Experimental observation of acoustic waves induced by an X-ray beam was first reported in 1985 when various metals were irradiated by a synchrotron X-ray beam, and the induced acoustic waves were detected by an ultrasound transducer. Despite promising results in these early studies, very little work was done regarding the use of X-ray-induced acoustics until recently. Recently, the present applicant, for the first time, proposed X-ray acoustic computed tomography (XACT) for radiation dosimetry. The applicant has found that the X-ray generated ultrasound signal is linearly related with X-ray dose deposition, which opened the possibility of using XACT imaging for radiation dose measurement during radiation therapy.

XACT imaging as a dosimeter also has been investigated using comprehensive computer simulation work, Monte Carlo dose calculations and acoustic wave transport techniques. These were developed to guide experimental investigations, and validated experimentally using simple geometries with metal block measurements. Later studies investigated using XACT to image dose distributions of various shapes and sizes in a homogeneous water tank. Experimental XACT images were obtained by keeping an immersion transducer stationary while a medical linear accelerator (LINAC) collimator was manually rotated. Transducer signals were acquired every 6 degrees around the radiation field and images were reconstructed using a simple back-projection algorithm. Profiles extracted from XACT images were compared to ion chamber measurements to verify the linear relationship between XACT image intensity and delivered radiation dose.

Figures 1A, 1B:
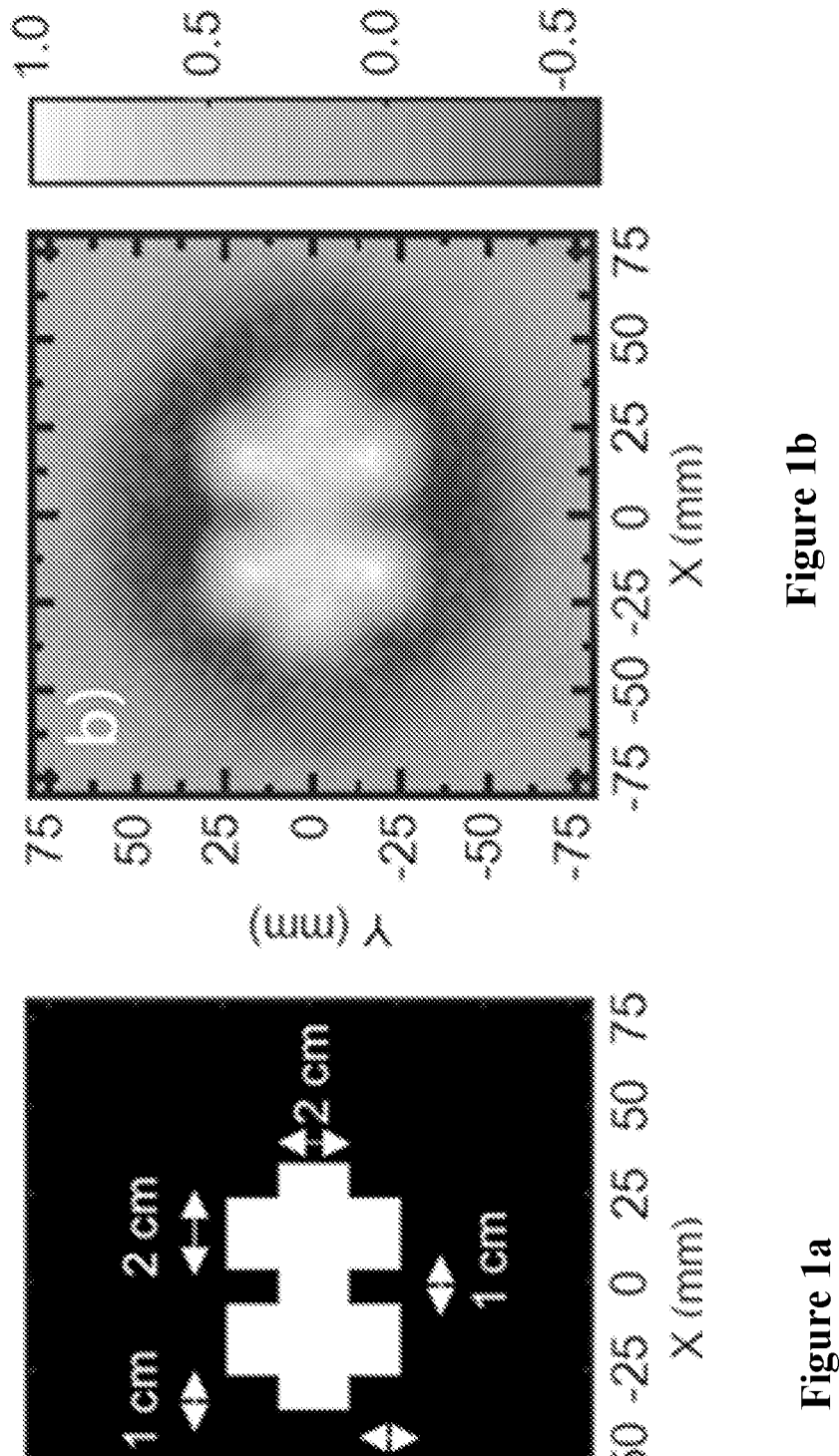
FIGS. 1a-1d illustrate example aspects of XACT imaging used for visualization photon beams for both water phantoms and soft tissue.

FIGS. 1a and 1b demonstrate the ability of an example XACT technique to image a puzzle piece shaped field in a water tank. More particularly, FIG. 1a illustrates the example puzzle piece radiation pattern that was used, and FIG. 1b illustrates an example acoustic image that was obtained using this example technique, with lighter areas showing more intense acoustic waves received by the transducer in response to the radiation pattern that was generated in the puzzle piece shaped field. A subsequent XACT characterization study demonstrated that XACT images of acceptable SNR can be obtained from dose levels as low as 11.6 mGy.

Figures 1C, 1D:
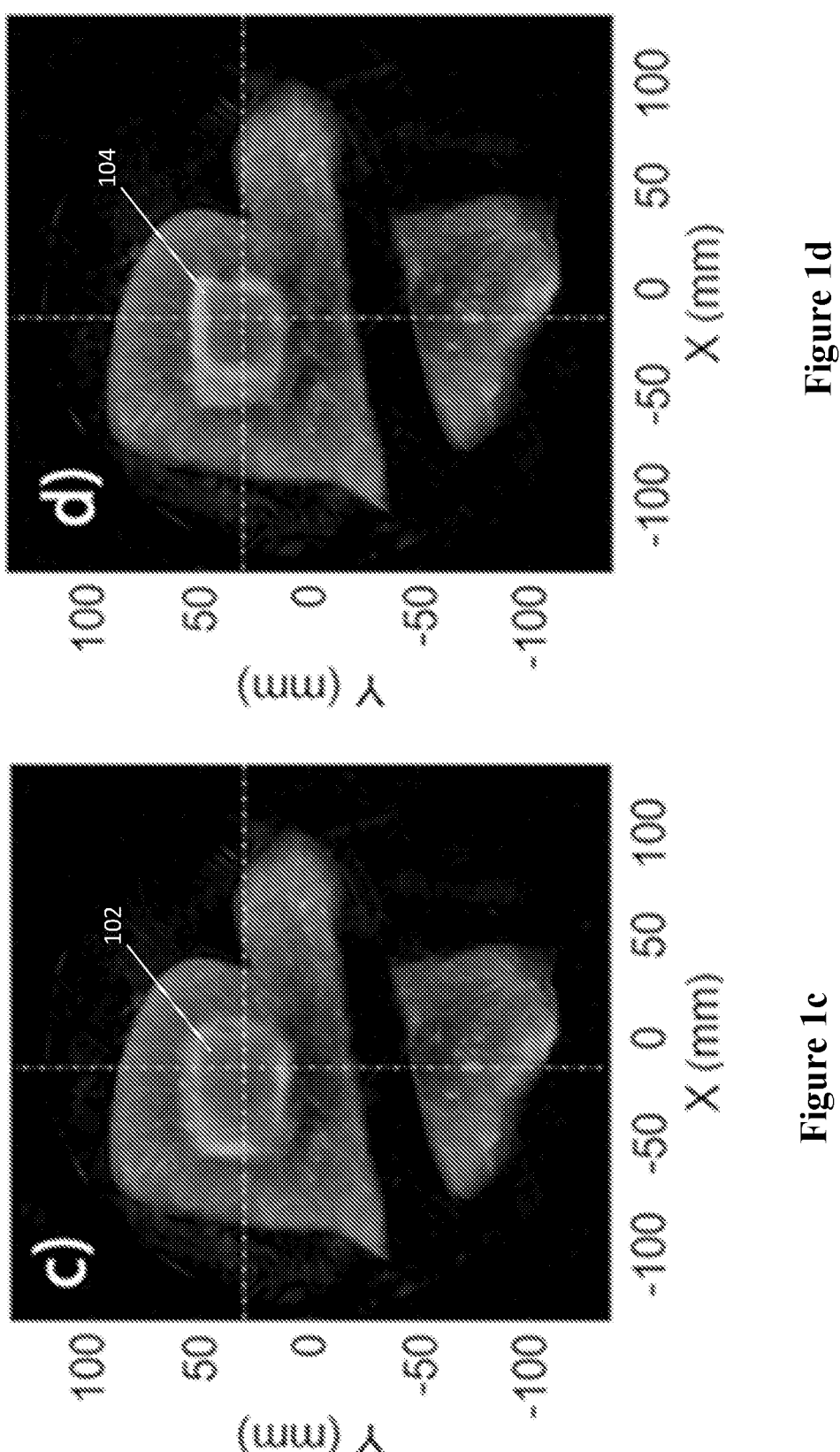

Recently, XACT with biological tissue phantoms as a sample have been demonstrated on veal liver. One example study employed conventional ultrasound imaging combined with XACT imaging to overlay the two images in such a way as to image the tissue 102 (FIG. 1c) and radiation beam (FIG. 1d) simultaneously. The beam intensity 104 inside fat tissue was clearly visible, and beam alignment could be monitored in addition to dose distribution, representing the first XACT deployment in a biological sample. These latest studies demonstrated the feasibility of using XACT as a viable dosimetry technique in a clinical radiotherapy environment.

However, due to the need to manually relocate the radiation source and/or acoustic transducer for each image, it currently takes tens of minutes to get a 2D image with an existing XACT imaging system, which renders real time mapping of the dose during radiation therapy impossible. Moreover, an existing XACT imaging system only works in a receiving model, and adding traditional pulse and echo ultrasound imaging has not been considered, much less successfully implemented for a clinical setting.

Figure 2:
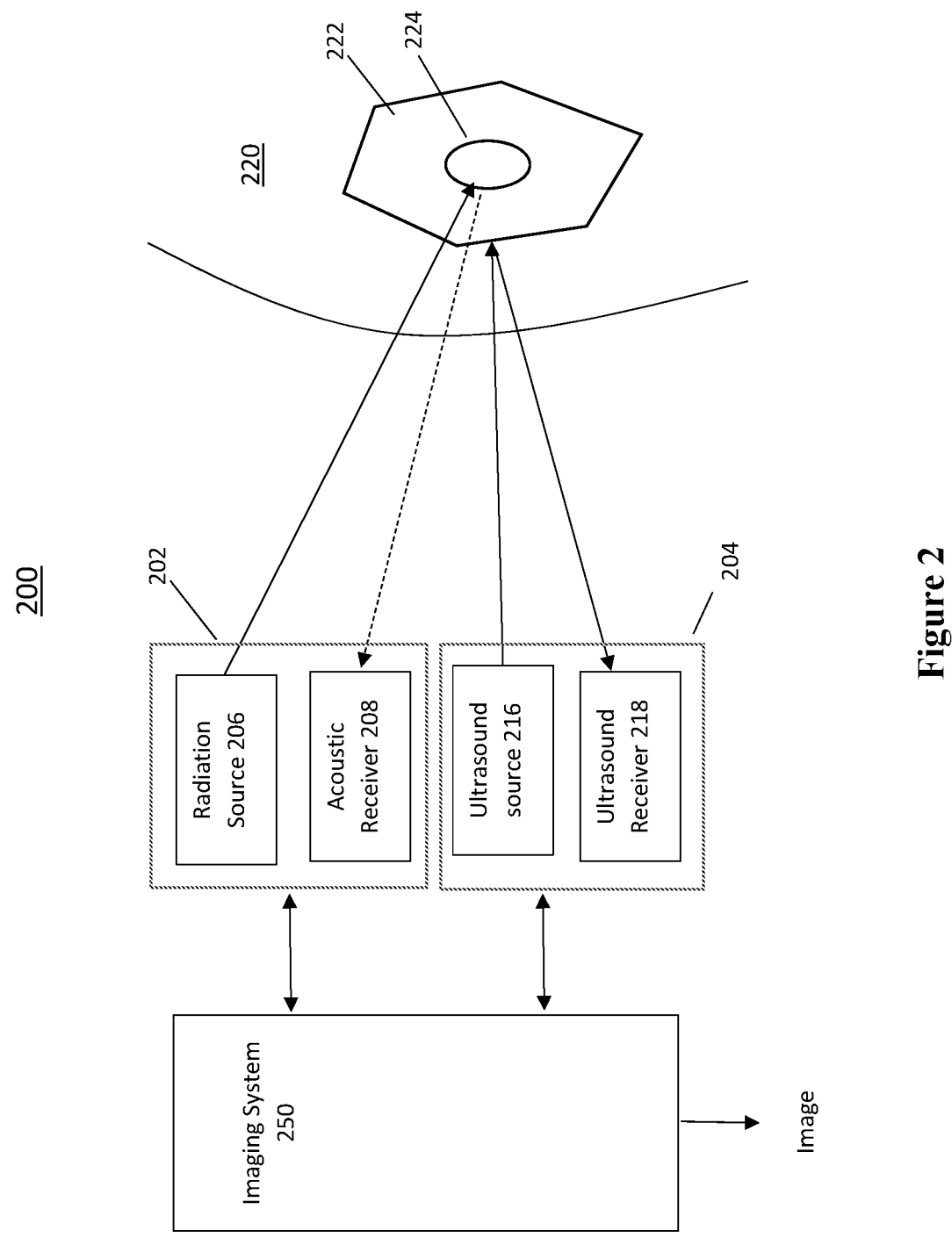
FIG. 2 illustrates example general aspects of a system and method according to the present embodiments.

The present disclosure provides systems and methods for generating both X-ray acoustic images and ultrasound images in real time. An exemplary system 200 associated with the present disclosure is shown in FIG. 2. As shown, this example system includes a radiation module 202 and an ultrasound module 204 that are both configured for generating and receiving signals, waves, beams, etc. associated with a subject 220 (e.g. living human/animal patient) having a treatment target 224 (e.g. cancer tumor) in surrounding tissue 222 (e.g. an organ). An imaging system 250 is configured to interact with modules 202 and 204 and to process the signals received by modules 202 and 204 so as to generate XACT/US images (e.g., real-time, 3D) according to the present embodiments.

As further shown, example radiation module 202 includes a radiation source 206 and an acoustic receiver 208. Radiation source 206 can include a conventional X-ray radiation treatment device such as a LINAC collimator. Acoustic receiver 208 can include a transducer capable of receiving acoustic signals 232 that are induced by the X-ray radiation, such as a piezoelectric transducer, a MEMS transducer, etc. Example ultrasound module 204 includes an ultrasound source 216 and an ultrasound receiver 218. Ultrasound module 204 can be implemented using similar techniques as used in existing pulse/echo ultrasound systems, as adapted for use in the present embodiments.

It should be appreciated that, although shown in a two dimensional space for ease of illustration, some or all of the various components of system 200 can be located in various planes or positions.

Figure 3:
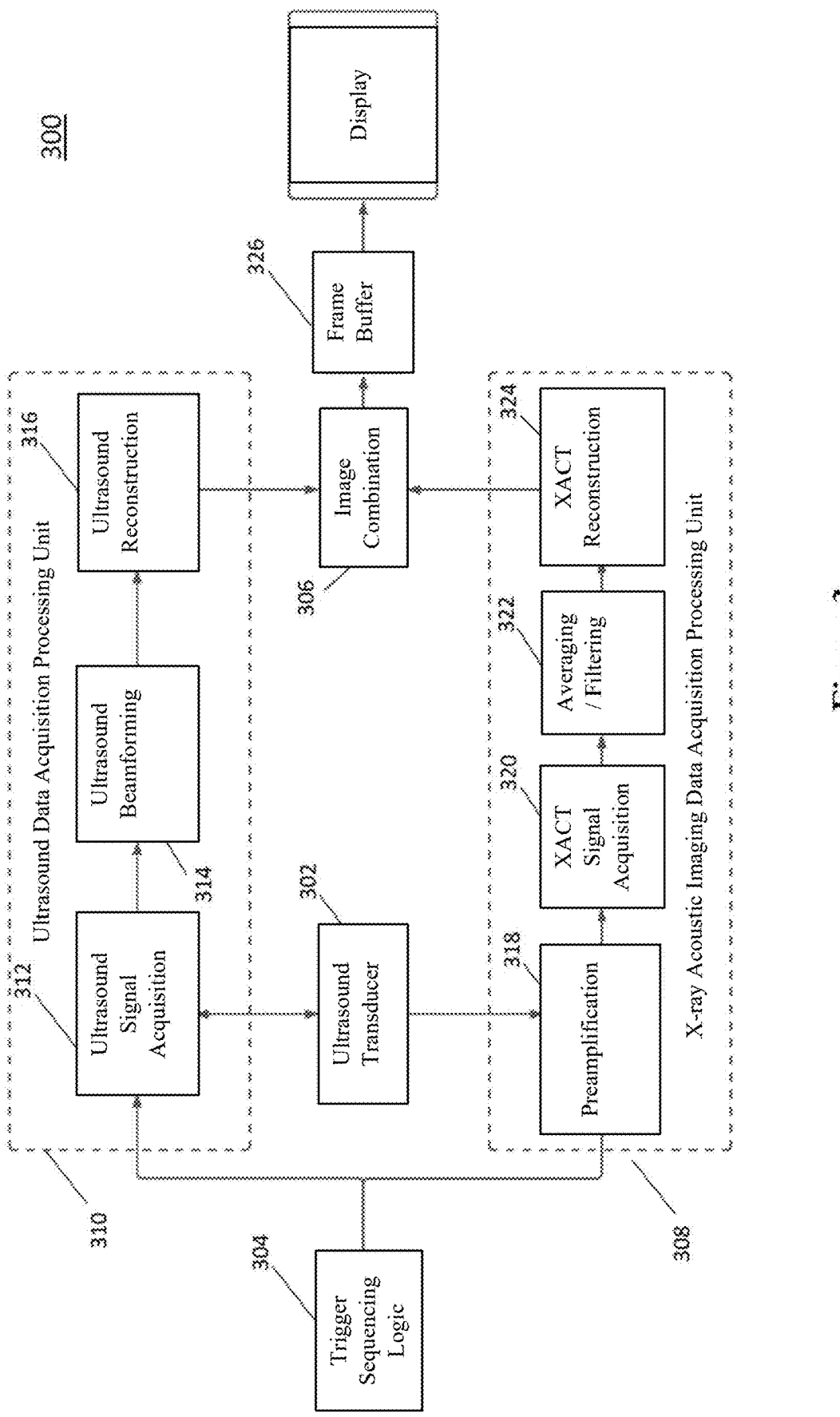
FIG. 3 illustrates an example system for generating X-ray acoustic images and ultrasound images in real time according to the present embodiments.

FIG. 3 illustrates an example system 300 according to the present embodiments in alternative detail. For example, in FIG. 3, a radiation source such as source 206 (e.g. X-ray radiation machine) is not shown. Meanwhile, in this example ultrasound source 216 and ultrasound receiver 218 are implemented together using conventional ultrasound transducer components, and further adapted with the functionality of acoustic receiver 208. Moreover, the functionality of imaging system 250 of system 200 is implemented in system 300 by one or more of 304, 306, 308 and 310 in FIG. 3, as will become more apparent from the descriptions that follow.

As shown in the example of FIG. 3, system 300 includes a two dimensional ultrasound array transducer 302 adapted to transmit ultrasound waves, receive ultrasound signal reflections from transmitted ultrasound waves, and receive acoustic signals generated from the x-ray radiation signals.

Example system 300 further includes a trigger sequencing logic device 304 that switches the ultrasound transducer connection between ultrasound emission/reception and x-ray acoustic signal acquisition. Example system 300 further includes an image combining unit 306 to receive and combine results from both x-ray imaging unit 308 and ultrasound unit 310 after reconstruction, In an exemplary embodiment, trigger sequencing logic device 302 switches the transducer connection based on the trigger signals from x-ray acoustic signal excitation source and the embedded ultrasound emission/reception, as explained in more detail below in connection with FIG. 4. To generate ultrasound reconstruction image by 310, the transducer signal is firstly collected by 312 during ultrasound reception window governed by the trigger sequencing logic switch. The collected signals are beamformed by an ultrasound beamformer 314 to create a series radio frequency signal. The radio frequency signals are reconstructed by 316 to create ultrasound images.

For X-ray acoustic imaging part 308, the transducer signal is collected immediately after x-ray firing trigger. To compensate for relatively small X-ray acoustic signals (e.g. 9 dB less than ultrasound echoes), a multi-channel preamplification stage 318 is built as the first stage of the X-ray acoustic imaging data acquisition processing unit 308. After preamplification, analog X-ray acoustic signals are acquired and converted to digital signals by 320, followed by an averaging/filtering stage 322. After averaging and filtering, the processed signal data can then be used for X-ray acoustic imaging reconstruction by 324.

An image combiner 306 is used to spatially resample averaged X-ray acoustic imaging reconstructions, so that they can be overlaid on top of the ultrasound reconstruction images. Temporal up-sampling can also be performed on one or both modality reconstructions, so that X-ray acoustic frames can be interpolated for each ultrasound frame for transmission to frame buffer 326.

The collecting speed of the radiation-induced acoustic signal is limited by the firing rate of the external radiation producing machine (e.g. 200 Hz). On the other hand, ultrasound transmission and echo reception are independent from an external source. Therefore, in an exemplary system, the trigger sequencing logic unit 304 is responsible for directing transducer input to the appropriate module 308/310 by sending out trigger signals to start echo-based ultrasound transmission and reception, and radiation-induced acoustic signal collection based on the timing of the external radiation producing machine's firing.

A typical trigger sequencing logic unit has three I/O ports: (1—external) Input trigger connection from radiation excitation source, e.g. X-ray machine; (2—Internal) Output trigger signal to echo mode Ultrasound module 310; and (3—Internal) Output trigger to radiation-induced acoustic data acquisition module 308.

Figure 4:
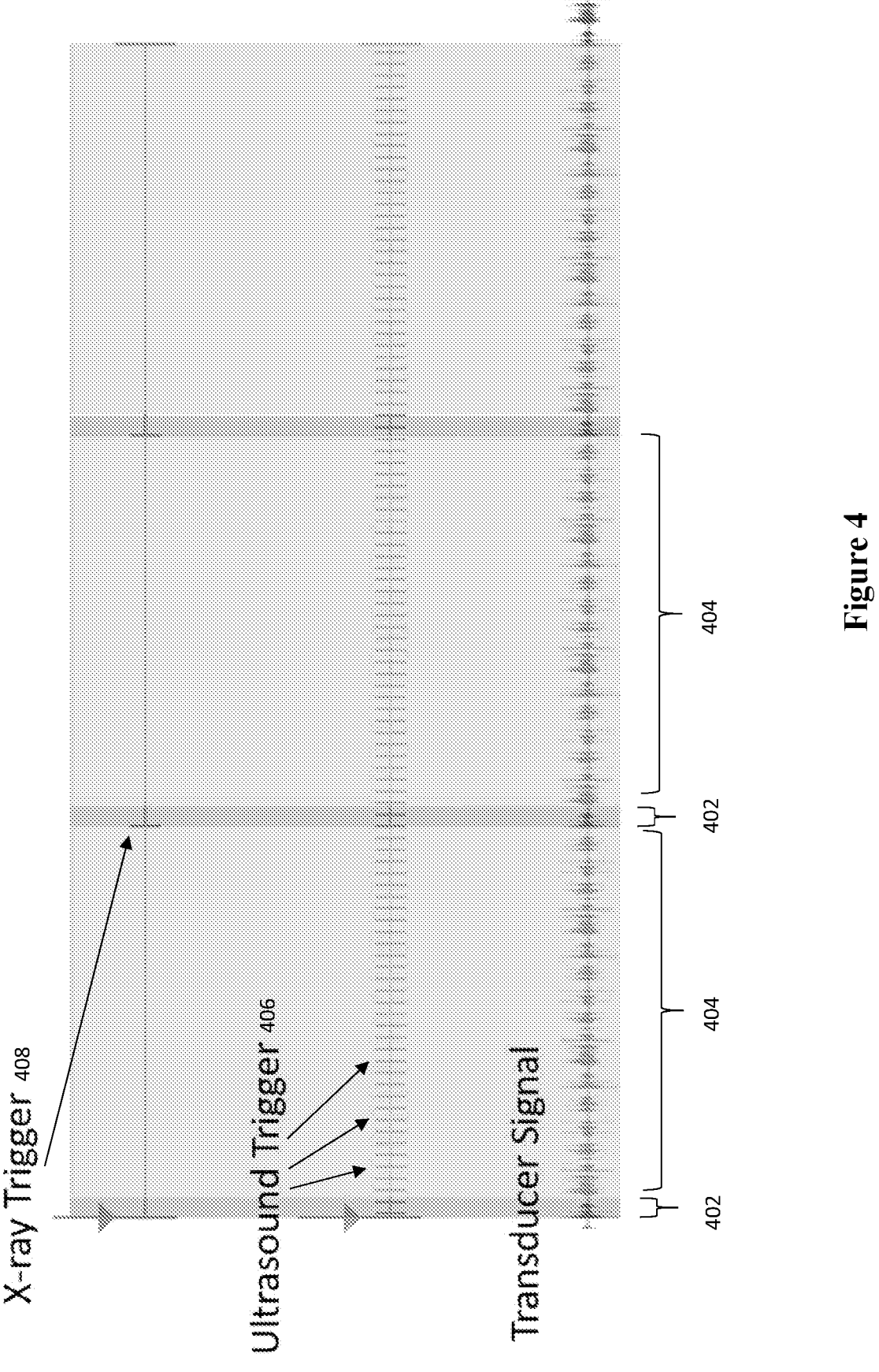
FIG. 4 is a timing diagram illustrating example aspects of switching an acoustic transducer connection based on the trigger signals from an x-ray acoustic signal excitation source and an embedded ultrasound emission/reception device according to embodiments.

An example timing diagram illustrating operation of an example trigger sequencing logic is shown in the FIG. 4. In an exemplary system, both the radiation-induced acoustic imaging module 308 and the echo-based ultrasound imaging module 310 are internally connected to the transducer 302 signal channels. As shown in FIG. 4, in a typical imaging scenario when radiation firing rate (e.g. 200 Hz) is slower than ultrasound imaging rate (e.g. 5 kHz), the trigger sequencing logic unit 304 will pause the emission/reception of the ultrasound during period 402 by stopping the trigger signals 406 to the echo-based ultrasound module 310. Instead, a trigger signal 408 will be sent to the radiation-induced acoustic imaging module 308 immediately to start the acquisition of radiation-induced acoustic signals during period 402. The echo-based ultrasound imaging module 310 remains inactive while the radiation-induced acoustic signals are being collected from transducer 304 and processed by 308. Thereafter, during period 404, the ultrasound trigger signals 406 are re-enabled, and ultrasound echo signals are collected from transducer 304 and processed by 310.

Example computing technology that can be used for implementing trigger sequence logic 302 includes but is not limited to: microcontroller units (MCU) or field programmable gate arrays (FPGA).

In an example system, the Image combing unit 306 has three following tasks, as described in more detail below.

Task 1: Color Mapping

To differentiate the reconstruction results from the different imaging modalities, different color mapping schemes will be applied in the first stage of image combing unit 306. The image combing unit will handle the assignment of individual pixel colors based on either a predefined color mapping scheme or a user selected color mapping choice.

Task 2: Reconstruction Up/Down Sampling for Co-Registration

Depending on the configuration of the ultrasound transducer array and the radiation-induced acoustic imaging reconstruction algorithms, the reconstruction images from echo-based ultrasound and radiation-induced acoustic imaging can have different resolutions. To solve this issue, an image combing processing unit is required to spatially up sample or down sample the radiation-induced acoustic imaging reconstruction results, so that physical reconstruction co-registration can be achieved for both imaging techniques in the same image frame on one display.

The real-time up sampling process can be achieved by using nonadaptive image interpolation techniques. Additionally, a spatial anti-aliasing prefiltering (e.g. spatial low pass filtering) is required for down sampling of the images. In both cases, the image combing unit will apply the appropriate image processing process based on the resolution differences between two reconstruction results.

Task 3: Temporal Interpolation

In the exemplar system design, there should be one fixed or limited range of frame rate settings for the final display, typically ranging from 1 Hz to 60 Hz, based on the operation needs.

Since the raw frame rate of the radiation-induced acoustic imaging depends on the firing rate of the radiation source (e.g. 200 Hz) and the amount of averaging performed before reconstruction, a temporal interpolation step is needed to numerically increase the frame rate of the reconstruction. The image combing unit will perform such task after the up/down sampling for co-registration process is completed.

Example technology that can be used for implementing image combining unit 306 includes but not limited to: field programmable gate arrays (FPGA).

In an exemplary system design, frame buffer 326 is a storage component that acts as a temporary frame data storage for the incoming displaying frames. It is preferred in the design so that a stable frame rate can be achieved for the final display.

Example technology that can be used for implementing frame buffer 326 includes but not limited to random-access memory (RAM). See, e.g., Vaishali Patel and Prof Kinjal Mistree, "A Review on Different Image Interpolation Techniques for Image Enhancement," International Journal of Emerging Technology and Advanced Engineering, vol. 3, no. 12, December 2013.

In an exemplary XACT/US system, ultrasound transducer array 302 is responsible of receiving and transmitting ultrasound waves, and is also capable of receiving acoustic signals generated by the X-ray beam. Such ultrasound transducer array has its output internally connected to both the echo-based ultrasound imaging unit 310 and the radiation-induced acoustic imaging unit 308. The ultrasound array 302 can be any type in either linear or multi-dimensional form and should be swapped based on the imaging needs. One example design is based on piezoelectric elements arranged in a 16×16 2D Planar ultrasound transducer array, wherein each sensor is about 3 mm square, and the 256 sensors are spaced apart equally such that the overall size of the array is about 5 cm×5 cm.

Figure 5A:
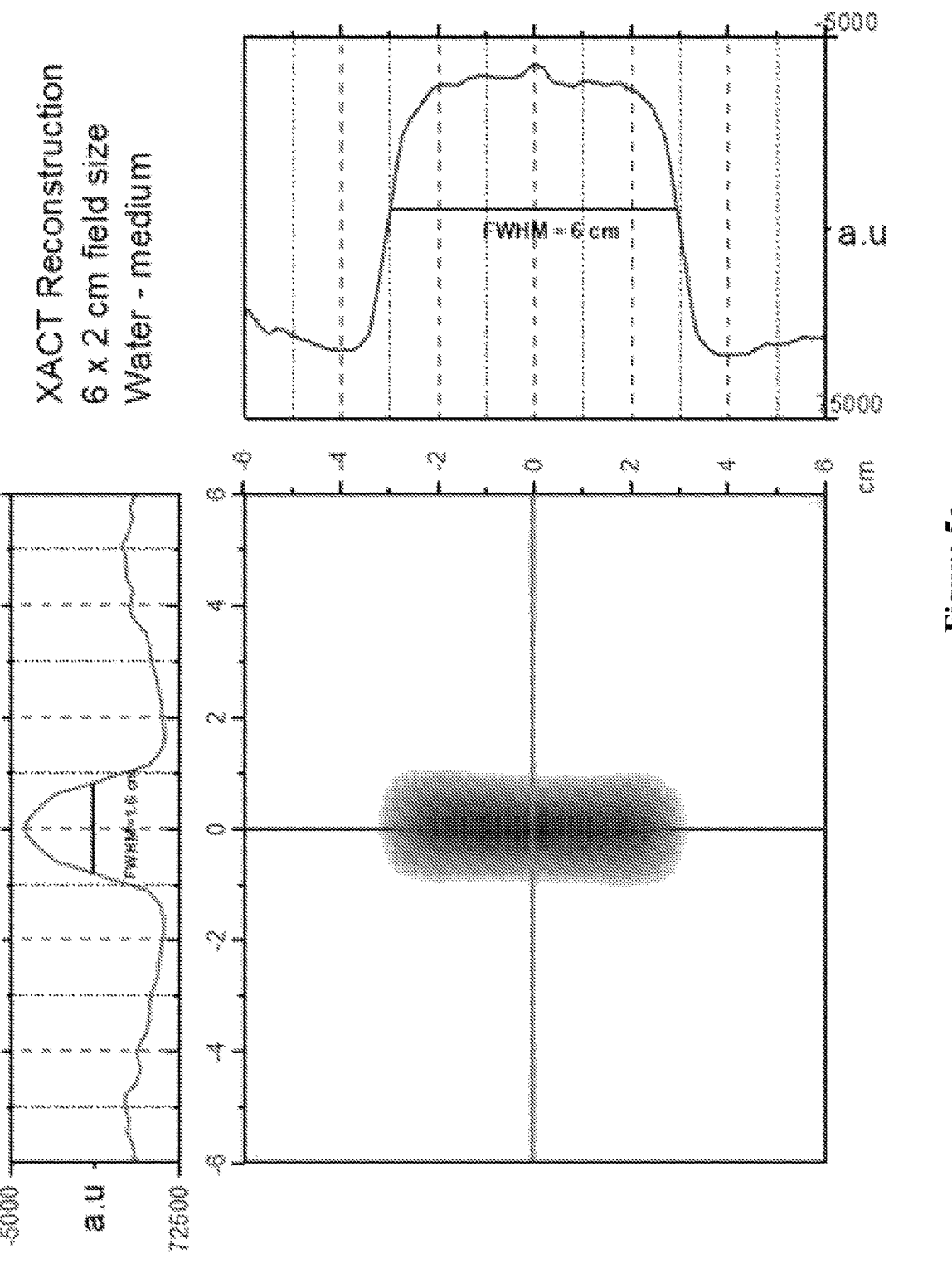
FIGS. 5a and 5b illustrate further example images generated by an exemplary XACT/US system according to embodiments.
Figure 5B:
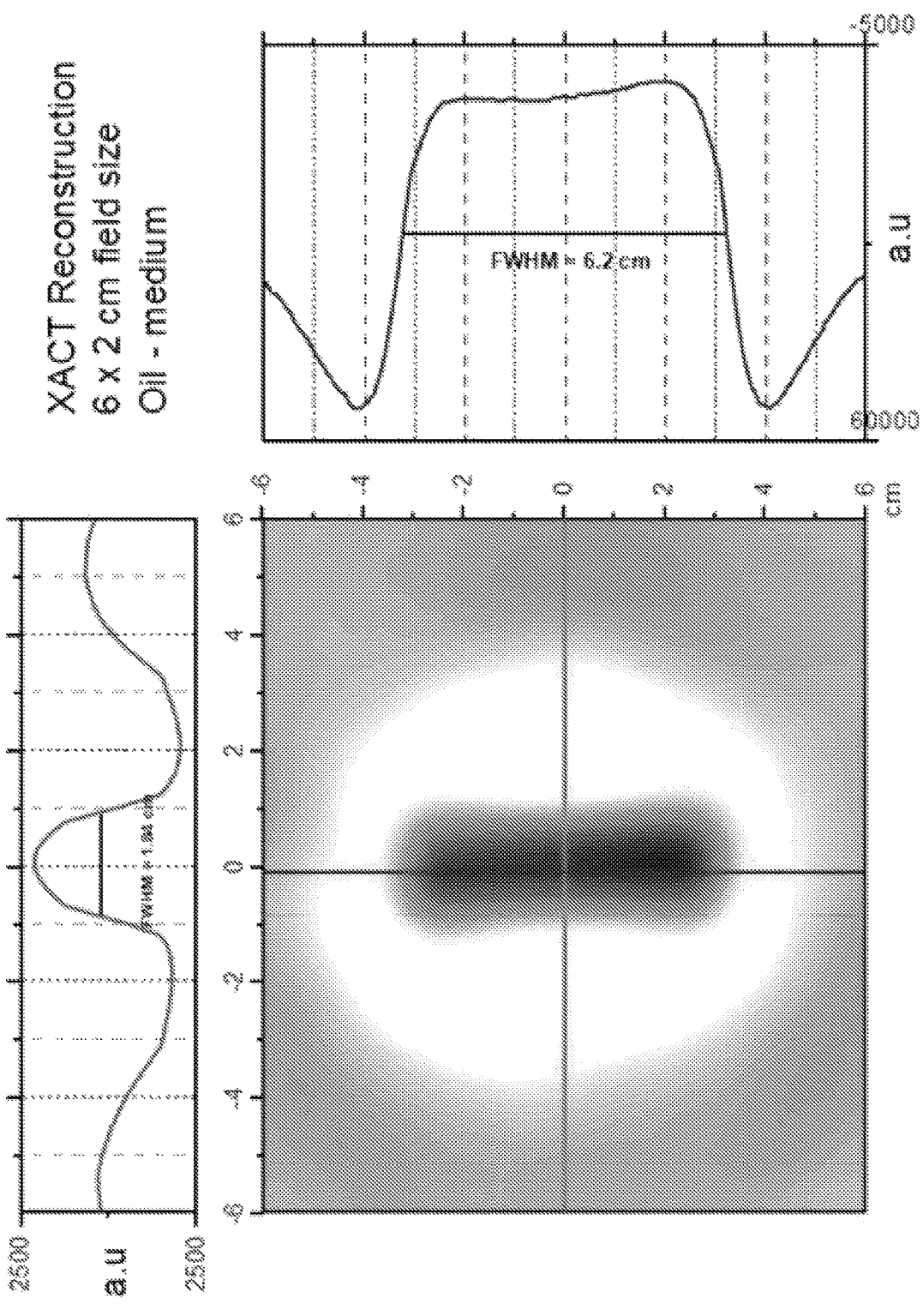

FIGS. 5a and 5b illustrate further example images generated by an exemplary XACT/US system according to embodiments with water and oil as a medium, for example.

According to certain aspects, the present embodiments will increase the precision of radiation delivery during radiotherapy by tracking the movements of the tumor and other tissues due to respiratory and other body motions and the position of the X-ray beam relative to those tissues while the treatment is being delivered in real time. The anatomical information of the tissue can be obtained through ultrasound imaging, while the XACT image acquired at the same time can provide the dosimetric information of the X-ray dose deposition in local tissue. The XACT/US imaging will provide additional information and it is highly valuable during external beam RT since it can greatly improve the accuracy in tumor targeting and largely mitigate the undesirable collateral damage to surrounding normal tissues, thereby leading to a better patient outcome. A 16×16 planar array provides 4D imaging capability for both XACT and ultrasound imaging The herein described subject matter sometimes illustrates different components contained within, or connected with, different other components. It is to be understood that such depicted architectures are illustrative, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably coupleable," to each other to achieve the desired functionality. Specific examples of operably coupleable include but are not limited to physically mateable and/or physically interacting components and/or wirelessly interactable and/or wirelessly interacting components and/or logically interacting and/or logically interactable components.

With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Further, unless otherwise noted, the use of the words "approximate," "about," "around," "substantially," etc., mean plus or minus ten percent.

The foregoing description of illustrative implementations has been presented for purposes of illustration and of description. It is not intended to be exhaustive or limiting with respect to the precise form disclosed, and modifications and variations are possible in light of the above teachings or may be acquired from practice of the disclosed implementations. It is intended that the scope of the invention be defined by the claims appended hereto and their equivalents.

What is claimed is:

1. A system for X-ray-induced acoustic computed tomography (XACT) comprising:
    a radiation source configured to apply a dose of radiation to a target in a living subject and to induce an acoustic signal associated with the dose of radiation;
    a two dimensional ultrasound array transducer;
    an ultrasound module configured to receive an ultrasound signal from the two dimensional array transducer and to generate an ultrasound image of tissue surrounding the target in the living subject; and
    an imaging module configured to combine the ultrasound image with an image representing the dose of radiation with respect to the surrounding tissue,
    wherein the two dimensional ultrasound array transducer is further configured to receive the acoustic signal induced by the radiation source, and
    wherein the radiation source is configured to apply the dose of radiation in correspondence with a X-ray trigger, and the ultrasound module is configured to generate an ultrasound pulse in correspondence with an ultrasound trigger, the system further comprising:

trigger sequencing logic that receives both the ultrasound trigger and the X-ray trigger and switches the two dimensional ultrasound array transducer between ultrasound signal reception in response to the ultrasound trigger and acoustic signal acquisition in response to the X-ray trigger.

2. The system of claim 1, wherein the ultrasound module generates the ultrasound image using pulse and echo ultrasound imaging.

3. The system of claim 1, further comprising an acoustic imaging unit coupled to receive the acoustic signal and including a processing unit configured to generate the image representing the dose of radiation.

4. The system of claim 3, wherein the acoustic imaging unit includes a preamplification stage to amplify the acoustic signal.

5. The system of claim 3, wherein the imaging module is configured to receive the ultrasound image from the ultrasound module, and to receive the image representing the dose of radiation from the acoustic imaging unit, and to output a combined image to a frame buffer for display.

6. A method of X-ray-induced acoustic computed tomography (XACT) comprising:

applying, by a radiation source, a dose of radiation to a target in a living subject and to induce an acoustic signal associated with the dose of radiation;

generating, by an ultrasound module, an ultrasound image of tissue surrounding the target in the living subject, wherein generating the ultrasound image includes receiving an ultrasound signal from a two dimensional ultrasound array transducer; and combining the ultrasound image with an image representing the dose of radiation with respect to the surrounding tissue, wherein the two dimensional ultrasound array transducer is configured to receive the acoustic signal induced by the radiation source, and wherein the radiation source is configured to apply the dose of radiation in correspondence with a X-ray trigger, and the ultrasound module is configured to generate an ultrasound pulse in correspondence with an ultrasound trigger, the method further comprising:

switching the two dimensional ultrasound array transducer between ultrasound signal reception in response to the ultrasound trigger and acoustic signal acquisition in response to the X-ray trigger.

7. The method of claim 6, wherein the ultrasound module generates the ultrasound image using pulse and echo ultrasound imaging.

8. The method of claim 6, wherein an acoustic imaging unit is coupled to receive the acoustic signal and includes a processing unit configured to generate the image representing the dose of radiation.

9. The method of claim 8, wherein the acoustic imaging unit includes a preamplification stage to amplify the acoustic signal.

10. The system of claim 1, wherein the two-dimensional array transducer comprises an array of transducer elements, each of the transducer elements being configured transmit ultrasound waves, receive ultrasound signal reflections from transmitted ultrasound waves, and receive acoustic signals generated from the x-ray radiation signals.

11. The method of claim 6, wherein the two-dimensional array transducer comprises an array of transducer elements, each of the transducer elements being configured transmit ultrasound waves, receive ultrasound signal reflections from transmitted ultrasound waves, and receive acoustic signals generated from the x-ray radiation signals.

* * * * *